US00PP12033P2

(12) United States Plant Patent
Taylor

(10) Patent No.: US PP12,033 P2
(45) Date of Patent: Aug. 7, 2001

(54) JUNIPER PLANT NAMED 'TAYLOR'S BLUE'

(75) Inventor: Allen Taylor, Boulder, CO (US)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 09/460,003

(22) Filed: Dec. 13, 1999

(51) Int. Cl.[7] ..... A01H 5/00

(52) U.S. Cl. ..... Plt./214
(58) Field of Search ..... Plt./214

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Juniper plant named 'Taylor's Blue', characterized by its very low-growing, procumbent plant habit; unique silvery-blue leaf color; relative ease of rooting; and tolerance to low temperatures.

1 Drawing Sheet

BACKGROUND OF THE INVENTION

The present invention relates to a new and distinct cultivar of Juniper plant, botanically known as *Juniperus horizontalis*, and hereinafter referred to by the cultivar name Taylor's Blue.

The new Juniper is a naturally-occurring whole plant mutation of an unidentified selection of *Juniperus horizontalis* (not patented). The new Juniper was discovered and selected by the Inventor in 1984, within a population of plants of the unidentified *Juniperus horizontalis* selection grown in a cultivated area in Lewis and Clark County, Montana. The new Juniper was selected on the basis of its unique silvery-blue foliage color and procumbent growth habit.

Plants of the new Juniper are lower-growing than plants of the parent selection, an unidentified selection of *Juniperus horizontalis*. In addition, foliage color of plants of the parent selection is typically green whereas foliage color of plants of the new Juniper is silvery-blue.

Asexual reproduction of the new cultivar by cuttings taken at Boulder, Colo., and Irvine, Calif., has shown that the unique features of this new Juniper are stable and reproduced true to type in successive generations.

SUMMARY OF THE INVENTION

Plants of the cultivar Taylor's Blue have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Taylor's Blue'. These characteristics in combination distinguish 'Taylor's Blue' as a new and distinct cultivar:

1. Very low-growing, procumbent plant habit.
2. Unique silvery-blue leaf color.
3. Relatively easy to root.
4. Tolerant to low temperatures.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Juniper. The age and the environmental conditions of the plants depicted in the photographs are the same as those disclosed in the detailed botanical description.

The photograph at the top of the sheet comprises a top perspective view of a typical plant of the new Juniper.

The photograph at the bottom of the sheet comprises a close-up view of typical lateral branches and leaves of the new Juniper.

DETAILED BOTANICAL DESCRIPTION

In the following description, color references are made to The Royal Horicultural Society Colour Chart except where general terms of ordinary dictionary significance are used.

Plants used for the description were one-year old and were grown in one-gallon containers under outdoor production conditions during the spring and early summer in Irvine, Calif.

Botanical classification: *Juniperus horizontalis* cultivar Taylor's Blue.

Parentage: Naturally-occurring whole plant mutation of an unidentified selection of *Juniperus horizontalis* (not patented).

Propagation: Relatively easy to root.

*Type.*—By cuttings.

*Time to initiate roots.*—About 40 days at 19° C.

*Time to develop roots* (*time to produce a rooted liner*).—About 90 days at 19° C.

*Root appearance.*—Fine, fibrous.

Plant description:

*Form.*—Low-growing, procumbent, spreading with long trailing branches, dense, and woody evergreen subshrub.

*Plant height.*—About 8 cm.

*Plant width.*—About 62 cm.

*Growth rate.*—Slow.

*Lateral branches.*—Quantity: Very freely branching; typically about 18 secondary laterals. Length: About 15 to 30 cm. Diameter, primary stem: About 7 mm.

Internode length: About 7.5 mm. Color: Young, 144B; woody, 177A.

*Foliage description.*—Leaves simple, scale-like, generally symmetrical, opposite and long-persisting. Leaves covered with waxy silvery-blue bloom. Leaves very durable and tolerant to drought stress. Length: About 3 mm. Width: About 1.75 mm. Shape: Narrow, scale-like. Apex: Acute. Base: Clasping; sessile. Margin: Entire. Texture: Glabrous. Color: Young foliage, upper surface: 147C. Young foliage, lower surface: Base color, 147D; covered with silvery-blue bloom, 188B to 188C to 190D. Mature foliage, upper surface: 137C. Mature foliage, lower surface: Base color, 137C; covered with silvery-blue bloom, 188B to 188C to 190D. Older leaves become mostly green, 137C, with subsequent development. Senesced leaves brown, 177A.

Cone description: Cone development not observed.

Disease resistance: Under commercial conditions, resistance to pathogens common to Junipers has been observed.

Low temperature tolerance: Plants of the new Juniper are hardy to zone 2b, USDA Hardiness Zone map.

It is claimed:

1. A new and distinct cultivar of Juniper plant named 'Taylor's Blue', as illustrated and described.

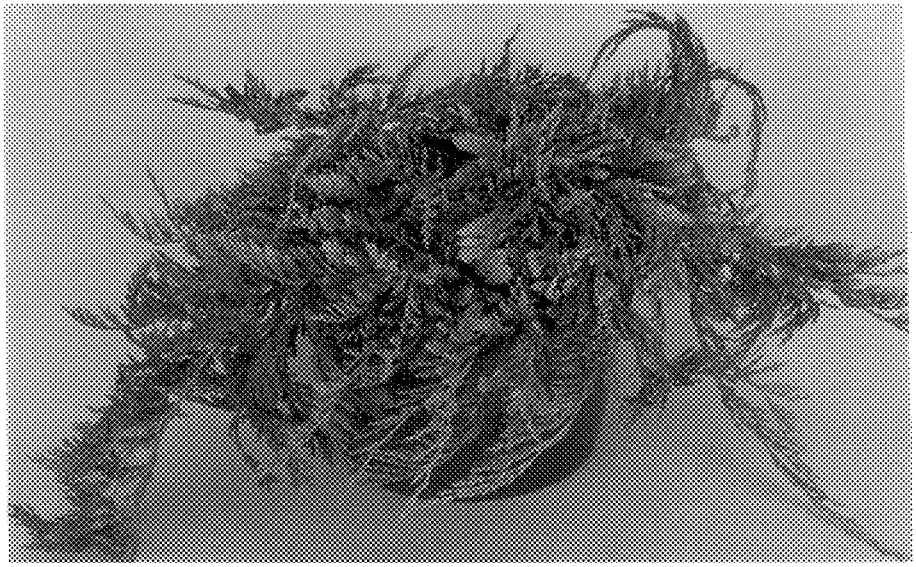
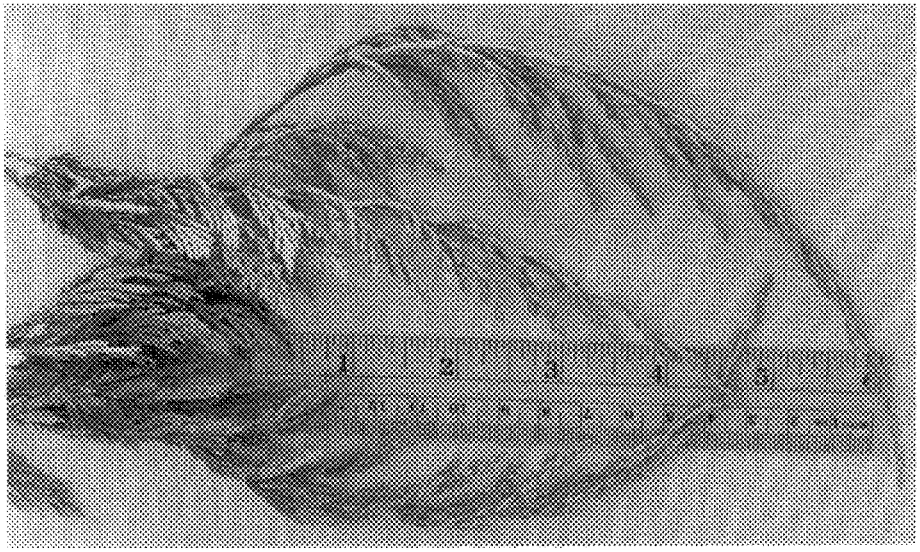

* * * * *